United States Patent [19]

Christensen et al.

[11] Plant 4,403

[45] Apr. 10, 1979

[54] DWARF PEACH TREE

[75] Inventors: Jack E. Christensen, San Dimas; Arnold W. Ellis, Bakersfield, both of Calif.

[73] Assignee: Armstrong Nurseries, Inc., Ontario, Calif.

[21] Appl. No.: 845,844

[22] Filed: Oct. 26, 1977

[51] Int. Cl.[2] ..... A01H 5/03

[52] U.S. Cl. ..... Plt./43

[58] Field of Search ..... Plt./43

*Primary Examiner*—Robert E. Bagwill

*Attorney, Agent, or Firm*—Andrew R. Klein

[57] ABSTRACT

A dwarf peach tree of upright-spreading bushy compact habit, having chilling requirements slightly higher than "Bonanza". The blossoms are single to semi-single, showy, moderate sized and pink. The crop borne is heavy. The freestone fruit is about 2½" in axial and transverse dimension and the flesh is firm, juicy, fine-grained and melting. It is characterized by a subacid flavor, and a capacity to retain its firmness and quality even somewhat beyond the full ripe state.

1 Drawing Figure

This invention relates to the discovery and asexual reproduction of a new variety of peach, originally propagated and asexually reproduced in Wasco, Calif. The description which follows will relate to a tree grown in that area. Specimens have also been grown in Ontario, Calif. The properties to be described are reproduced through successive propagations by budding.

The seed parent was an unnamed and undisseminated genetic dwarf freestone nectarine. The pollen parent was the genetic dwarf peach "Bonanza" (U.S. Plant Pat. No. 2,213).

Among the characteristics which distinguish this new genetic dwarf peach from its seed parent are, most notably, the fact that the new cultivar bears peaches while its seed parent bears nectarines. Furthermore, the mature height of the new cultivar is approximately only three-fourths of the mature height of the seed parent. The quality of the fruit of the new cultivar is considerably better than the fruit quality of its seed parent.

The new variety differs significantly from its pollen parent, the genetic dwarf peach "Bonanza", particularly in these respects: The leaf margins on the foliage of the new cultivar are nearly crenulate, whereas the leaf margins on the foliage of Bonanza are finely serrate. The fruit of the new cultivar has a more highly colored skin, and is therefore more attractive than the fruit of its pollen parent. Still further, and most importantly, the new cultivar displays a noteworthy improvement in flesh quality as compared to its pollen parent. The flesh of the fruit is firm, juicy and fine-grained, and it retains this characteristic even until somewhat after the fruit becomes fully ripe. The fruit of the pollen parent, Bonanza, is less firm, even when barely eating ripe, and loses its firmness rather quickly.

It is to be noted that both parents of the new variety were genetic dwarf trees, so that budwood of the new variety can confidently be grown on any of several root stocks without risk of losing the dwarf characteristic.

Throughout this specification, color names beginning with a small letter signify that the name of that color, as used in common speech, is aptly descriptive. Color names with capital letters designate values based upon the Nickerson Color Fan, put out by Munsell Color Co.

The accompanying drawings show a typical leaf cluster and also a single mature leaf and its attachment. Also shown are views of the fruit, from above and below. The depth of skin coloration will be appreciated.

A fruit split in the plane of the suture is also shown, one view showing the pit cavity empty and the other, filled.

TREE

The growth habit of the new variety is vigorous and upright-spreading. It is a compact bushy dwarf, characterized by internodes of the stem ranging from approximately ¼ to ½" in length. It has leaves of a relatively normal or standard size and appearance for peaches.

The chilling requirement is slightly higher than that of the "Bonanza" dwarf peach, above mentioned. In Southern California, it begins to bear at a relatively early age for peaches, and it bears a heavy crop.

The surface texture of current growth is smooth at first with small minute lenticels. With age, some large, cracked, slightly raised lenticels appear towards the base of the more vigorous shoots. The color is at first green, or reddish on the exposed surfaces, with lenticels appearing as small off-white dots; all tending to brown with age. Two-year old wood has a surface texture which is somewhat bumpy and rough, from raised nodes and buds and their closeness together on the stem. Otherwise, internodes are generally smooth with some slightly raised lenticels and irregular longitudinal striations. The color is generally brown, sometimes reddish brown.

The surface texture of old wood manifests less bumpiness and less rough effect from the nodes and buds, as they are covered by the growth of the stem as diameter increases. They become more smooth overall, with a moderate number of raised lenticels and some small longitudinal fissures. The color is gray to grayish brown or reddish brown on the more exposed surfaces.

The leaves vary in size from about 6½ to 9" in length and 1 to 1½ "in width. They are lanceolate in shape, with the apex acuminate. The upper surface of the mature leaf is between Moderate Olive Green, 5GY4/3, and Grayish Olive Green, 5GY3/2. The under surface of the mature leaf is between Moderate Yellow Green, 2.5GY5/5, and Moderate Olive Green, 2.5GY4/3. The petiole is of medium length and thick to medium thickness. The leaf margins are nearly crenulate, rather than serrate, and are glandular. The glands are mixed globose and reniform, of small to medium size, usually two or three in number, but sometimes from four to six.

They are borne both on the petiole and on the base of the blade.

The vegetative buds are small in size and, unless compressed between flower buds, are ovoid in shape. The scales are of moderate length with thick pubescence, and the color is dark brown.

FLOWERS

The dormant flower buds are ovoid in shape with pubescent scales. They are dark brown, with pubescence giving a whitish effect. The dates of first bloom have varied from February 25 to March 1, and the dates of full bloom from March 10 to March 17, depending upon weather variations from year to year. The flowers are showy when fully open and they are of medium size, about 1½" in diameter. They are cupped in form with single to semi-single petalage, usually 5 to 8 petals.

The color of the open flower is between Pale Pink 2.5R9/3, and Pale Purplish Pink, 7.5RP9/12. With age, the color darkens near the point of attachment, generally towards a color between Strong Purplish Red, 10RP5/12, and Strong Purplish Pink, 7.5R7/10, but lightens to near white near the margins.

FRUIT

The fruit generally ripens in the latter half of June at Wasco, Calif. The first ripening dates have ranged from June 21 to June 29. Usually, the fruit ripens about two weeks after the Bonanza genetic dwarf peach. A description of the fruit when eating ripe follows:

The size is slightly variable but generally medium, ranging from 2¼" to 2⅝" in axial diameter, and from 2¼" to 2⅝" in transverse diameter, both in the suture plane and at right angles to the suture plane. It is relatively uniform in shape, being nearly symmetrical and globose. The suture ranges from inconspicuous to distinct, and from shallow to medium depth. It extends from the base to the apex with a slight depression beyond the pistil point. The ventral surface is slightly rounded and sometimes slightly lipped toward the base. The lips are relatively equal.

The stem cavity is flaring, elongated in the suture plane with the suture showing on both sides. It is from about ⅜" to ½" both in depth and in width. The base is rounded to truncate, and the apex short and with the pistil point apical. The stem is of medium caliper and glabrous. It shows medium adherence to the stone, and is about ¼" long.

SKIN

The skin is of medium thickness and tender texture. In tenacity to the flesh it may be classified as free. Pubescence is moderate and of medium length. The ground color varies from near Brilliant Greenish Yellow, 10Y9/9, to near Brilliant Yellow, 5Y9/9. It is moderately to heavily overlaid with flecks, streaks, mottling and blushes of from near Strong Red, 5R4/12, to near Dark Red, 5R3/7.

FLESH

The flesh is fine-grained and melting in quality, with many fine tender fibers. It retains its firmness and fine-grained quality to a significant degree even when overripe. The aroma is pronounced, and the flavor subacid. There is little or no apparent astringency.

The color of the flesh is near Moderate Orange Yellow, 10YR8/10. The surface of the pit cavity is between Brilliant Yellow, 2.5Y9/9, and Vivid Yellow, 2.5Y8/12, in color, with some small flecks of near Strong Red, 5R4/12.

STONE

The stone parts freely from the flesh, although it sometimes adheres slightly along the ventral edge. It is of medium length, about 1½", with a width of approximately 1" and a thickness of about ¾". It is oval in form and cuneate towards the apex, the base being somewhat oblique. The hilum is broad, nearly round to oval. The apex is rounded to acuminate. The sides vary from equal to unequal. They are irregularly furrowed toward the apex and near the base, pitted from the base to past the center point, and ridged toward the apex. The ventral edge is of medium thickness generally without wing. The dorsal edge is narrow, with a deep groove to beyond center and interrupted ridges on either side. The color of the stone is between Moderate Orange Yellow, 7.5YR8/8, and Strong Orange, 5YR6/11. There is a moderate tendency to split in a dry season.

The tree may be used as a decorative shrub for the landscape. The fruit has potential value for market use, and is suitable for dessert, for canning, and for culinary purposes generally. The keeping and shipping qualities of the fruit are both good.

We claim:

1. A new variety of dwarf peach tree, substantially as illustrated and described, and having leaves with almost crenulate margins, showy pink blossoms, and freestone fruit, which has a skin of brilliant yellow overlaid with variegated strong to dark red coloration, the fruit, being especially characterized in the firm, juicy, fine-grained and melting character of its flesh, which retains these properties even somewhat beyond a fully-ripe state.

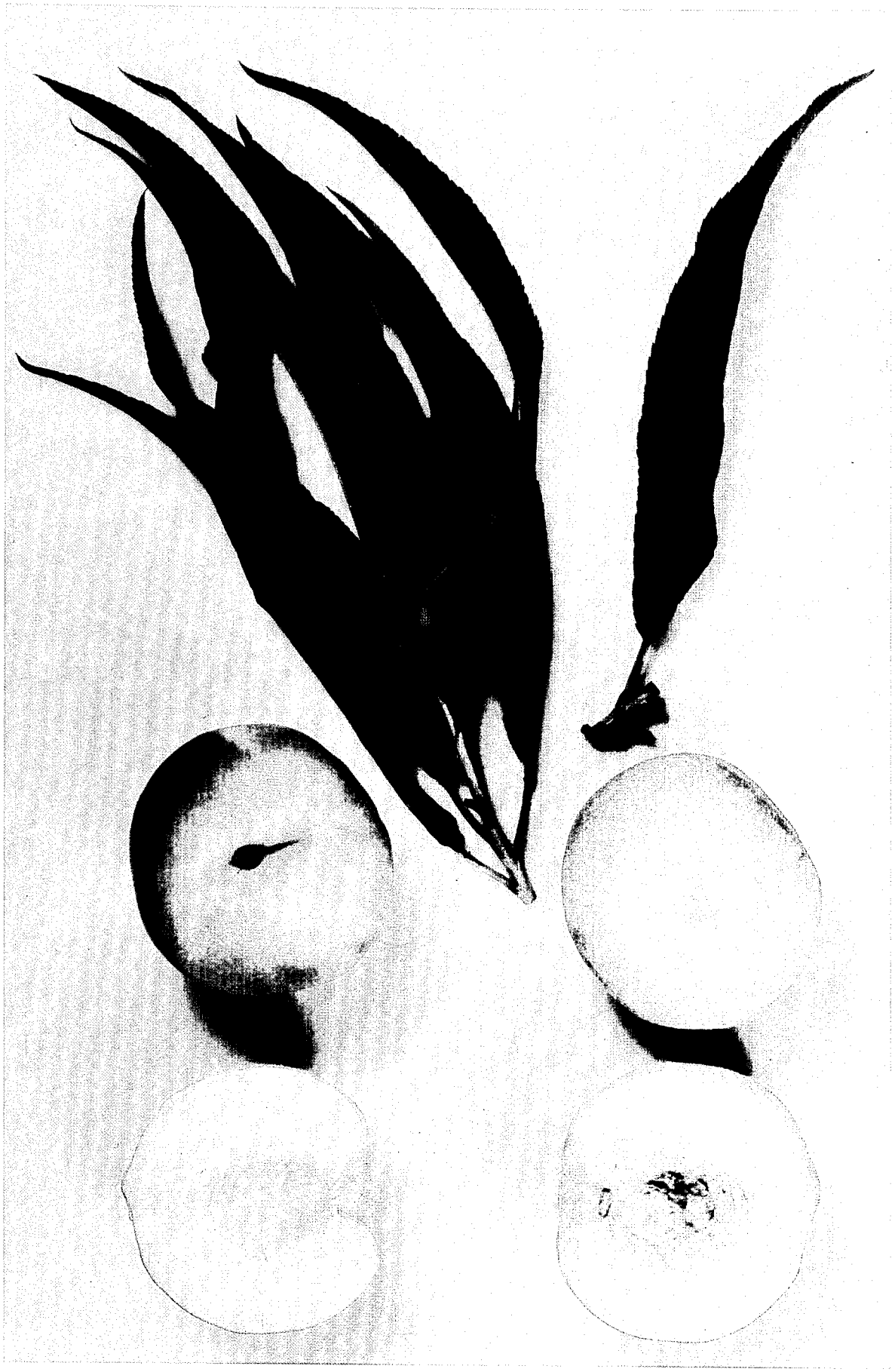

* * * * *